United States Patent [19]

Mattson et al.

[11] Patent Number: 5,098,904
[45] Date of Patent: Mar. 24, 1992

[54] CEREBRAL FUNCTION ENHANCING PYRIMIDINYL DERIVATIVES

[75] Inventors: Ronald J. Mattson, Meriden; Robert Mayol, Durham, both of Conn.; Michael E. Brady, Baldwinsville, N.Y.

[73] Assignee: Bristol-Myers Squibb Company, New York, N.Y.

[21] Appl. No.: 544,570

[22] Filed: Jun. 27, 1990

[51] Int. Cl.$^5$ .............. A61K 31/505; A61K 31/445; C07D 401/14
[52] U.S. Cl. ...................... 514/256; 514/269; 544/298; 544/326; 544/329
[58] Field of Search ............... 544/298, 326, 329; 514/256, 269

[56] References Cited

U.S. PATENT DOCUMENTS

| | | | |
|---|---|---|---|
| 3,398,151 | 8/1968 | Wu et al. ............................ | 260/268 |
| 3,558,777 | 1/1971 | Wu et al. ............................ | 424/250 |
| 3,717,634 | 2/1973 | Wu et al. ............................ | 260/256.4 N |
| 3,907,801 | 9/1975 | Wu et al. ............................ | 260/268 BC |
| 3,976,776 | 8/1976 | Wu et al. ............................ | 424/251 |
| 4,361,565 | 11/1982 | Temple, Jr. et al. ............. | 424/250 |
| 4,411,901 | 10/1983 | Temple, Jr. et al. ............. | 424/250 |
| 4,423,049 | 12/1983 | Temple, Jr. ....................... | 424/251 |
| 4,524,206 | 6/1985 | New et al. ........................ | 544/230 |
| 4,668,687 | 5/1987 | Yevich et al. .................... | 514/252 |
| 4,826,843 | 5/1989 | Mattson et al. .................. | 514/252 |

FOREIGN PATENT DOCUMENTS 2023594 1/1980 United Kingdom .

OTHER PUBLICATIONS

Butler et al., "Amnesia-Reversal Activity, etc." *J. Med. Chem.*, 1984, 27, 684–691.
Malawska, et al., "Synthesis and Pharmacological, etc." *Pol. J. Pharmacol. Pharm.*, 1982, 34, 373–382.

Primary Examiner—Patricia L. Morris
Attorney, Agent, or Firm—William T. Han

[57] ABSTRACT

A series of pyprimidinyl compounds of formulae I, II and III;

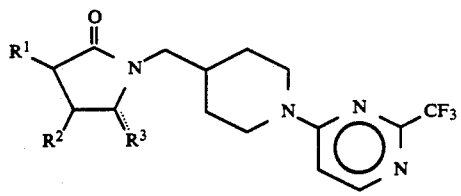

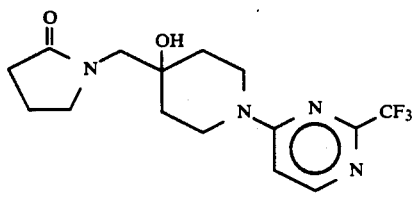

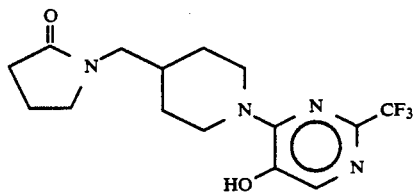

wherein $R^1$ and $R^2$ are independently selected from hydrogen and hydroxy;
$R^3$ is selected from hydrogen, hydroxy, or oxo, with the proviso that $R^3$ can only be oxo when $R^1$ and $R^2$ are hydrogen, and further that $R^1$, $R^2$, and $R^3$ cannot all be hydrogen or hydroxy at the same time; and
the solid and dotted lines refer to either a double covalent bond or a single covalent bond with another hydrogen atom covalently bonded to the carbon terminus end.

The compounds of this invention possess cognition and memory enhancing activity.

15 Claims, 3 Drawing Sheets

CEREBRAL FUNCTION ENHANCING PYRIMIDINYL DERIVATIVES

BACKGROUND OF THE INVENTION

This invention generally pertains to heterocyclic compounds having drug and bio-affecting properties and to their preparation and use. In particular, the invention is concerned with oxygenated derivatives of 1-[[1-[2-(trifluoromethyl)-4-pyrimidinyl]-4-piperidinyl]-methyl]-2-pyrrolidinone, or more commonly known as BMY-21502. The compounds of this invention are cerebral function enhancers useful in treating various dementias due to degenerative processes as well as in enhancing memory and learning.

Clinical aspects of various degenerative dementias, as well as the socioeconomic problems they cause in affected populations, are well known to those skilled in the art. One will also appreciate that various drug treatments of these disorders are currently under study. Among such drugs are a class of drugs known as nootropic agents or, more commonly, cognition enhancers; some of are currently undergoing clinical evaluation in patients diagnosed as having Alzheimer's disease, a serious and fairly common CNS disorder of the elderly. Chemically, these drugs under clinical study are members of a class of N-substituted 2-pyrrolidinone derivatives of structure 1.

a: X=H; R=—CH$_2$CONH$_2$ (piracetam)
b: X=OH; R=—CH$_2$CONH$_2$ (oxiracetam)
c: X=H; R=—CH$_2$CONH[CH$_2$]$_2$N[CH(CH$_3$)$_2$]$_2$
d: X=H;

(aniracetam)

For a representative reference describing the testing and properties of a member of this series, see: Butler, et al., *J. Med. Chem.*, 27, pp. 684-691 (1984). Preliminary clinical results of this class of agents indicate that the drugs may have some beneficial effects in treating senile dementias in the elderly.

A series of patents disclose a number of compounds with structures corresponding to formula 2.

wherein X is usually C$_{2-4}$ substituted or unsubstituted alkylene; Y is carbonyl or methylene; A is a bridging moiety such as alkylene, alkanoyl, alkyleneamidoalkylene, and the like; W is nitrogen; and B is a pyrimidinyl, pyridinyl, or benzisothiazolyl ring system. Members of this series are reported to have psychotropic, anxiolytic, antiemetic, tranquilizing, cognitive enhancing, as well as other nootropic activities. For more detailed disclosure of these compounds, see: Yevich and Mattson, U.S. Pat. No. 4,668,687 issued May 26, 1987; Wu, et al., U.S. Pat. No. 3,717,634 issued Feb. 20, 1973; Temple, U.S. Pat. No. 4,423,049 issued Dec. 27, 1983; and New and Yevich, U.S. Pat. No. 4,524,206 issued June 18, 1985.

Other subject matter related to formula 2 compounds was disclosed by Malawska, et al., in "Synthesis and Pharmacological Properties of Some 2-Pyrrolidinone Mannich Bases" in the *Polish Journal of Pharmacology*, 34, pp. 373-382 (1982). They described a series of compounds, of which one subclass is represented by structural formula 3, which reportedly display analgesic properties as well as weak anti-inflammatory action, wherein X is hydrogen or chlorine.

The most relevant art is believed to be in the patent to Mattson, et al., U.S. Pat. No. 4,826,843 issued May 2, 1989, wherein compounds of general formula 4 were disclosed as having cognition and memory enhancing activities.

For formula 4, X is an ethylene chain or 1,2-benzo ring; Y is carbonyl or methylene; R$^1$ is hydrogen or lower alkyl; and Z is an R$^2$, R$^3$-disubstituted diazinyl ring selected from pyridazine, pyrimidine, and pyrazine ring systems. A preferred compound of the series was 1-[[1-[2-(trifluoromethyl)-4-pyrimidinyl]-4-piperidinyl]-methyl]-2-pyrrolidinone (4a), hereinafter referred as BMY-21502.

BMY-21502 is currently under clinical evaluation for the treatment of memory and cognitive disorders.

SUMMARY OF THE INVENTION

The present invention is concerned with compounds of formula I and its pharmaceutically acceptable salts, wherein $R^1$ and $R^2$ are independently selected from hydrogen and hydroxy;

$R^3$ is selected from hydrogen, hydroxy, or oxo, with the proviso that $R^3$ can only be oxo when $R^1$ and $R^2$ are hydrogen, and further that $R^1$, $R^2$, and $R^3$ cannot all be hydrogen or hydroxy at the same time; and the solid and dotted lines refer to either a double covalent bond or a single covalent bond with another hydrogen atom covalently bonded to the carbon terminus end.

Another aspect of this invention relates to the compound of formula II and its pharmaceutically acceptable salts.

A further aspect of this invention relates to the compound of formula III and its pharmaceutically acceptable salts.

Representative compounds of this invention were selected for testing and were shown to display cognition enhancing action. Thus, as another aspect of the invention, compounds of the series can be incorporated into pharmaceutical compositions for use in patients afflicted with senile dementias.

BRIEF DESCRIPTION OF THE DRAWINGS

FIG. 2. EI mass spectrum of TMS derivative of a dog urinary BMY-21502 metabolite from peak 2a.

DETAILED DESCRIPTION OF THE INVENTION

BMY-21502 is an orally active agent for the treatment of memory and cognitive disorders including senile dementia and Alzheimer's disease. While its mechanism of action is not completely known, beneficial effects of BMY-21502 have been demonstrated in behavioral paradigms, autoradiographic studies, cell culture studies, and electrophysiologic examination of hippocampal neurons in rat brain slices.

Metabolism of a drug molecule through an oxidative pathway is common. For general background, cf: "Pharmacokinetics," Peter G. Welling, ACS Monograph 185, American Chemical Society, Washington, DC, 1986. Metabolites of nootropic agents may be biologically active in their own right. Oxiracetam, as an example, has been shown to be the major metabolite of piracetam.

In its broadest aspect, the instant invention is concerned with oxygenated derivatives of BMY-21502 and the identification that some of these derivatives as metabolites. The assignment of molecular structure of these metabolites was confirmed by comparison of spectral and chromatographic data with those of synthesized putative metabolites. Processes for preparation of the derivatives of BMY-21502 are also described herein. Furthermore, this invention relates to the discovery that these BMY-21502 derivatives possess nootropic activity.

Compounds of the present invention can be obtained either by 1) chemical synthesis or
2) isolation of metabolites from plasma or urine of a mammal fed with BMY-21502.

Isolation of metabolites can be achieved by commonly used chromatographic methods, such as by High Pressure Liquid Chromatography (HPLC) as described in the Description of Specific Embodiments section. For general chromatographic techniques, see: "Introduction to Modern Liquid Chromatography," L. R. Snyder & J. J. Kirkland, John Wiley & Sons, Inc., 1979.

Synthesis

Various Formula I compounds can be synthesized using the following routes or appropriate modifications thereof.

Route 1

A compound of Formula I of the present invention, wherein $R^1$ and $R^3$ are hydrogen and $R^2$ is hydroxy (Ia), can be prepared by a process which comprises the consecutive steps of:

a) Reacting 4-chloro-2-(trifluoromethyl)pyrimidine (IV) with isonipecotamide (V) to afford compound VI.

V

VI b) Eliminating water from compound VI using a suitable dehydrating agent such as phosphorus oxychloride to afford nitrile VII.

VII c) Catalytically hydrogenating the nitrile group in compound VII to afford amine VIII.

VIII d) Reacting compound VIII with an acetate IX to yield a compound of formula X,

ZCH$_2$—CO$_2$R    IX

X wherein Z is chlorine, bromine, iodine, or other leaving groups such as tosylate, mesylate, and the like; and R is a primary C$_{1-4}$ alkyl group.

e) Reacting a compound of formula X with a malonyl derivative of formula XI, wherein Y is chlorine or bromine; and R is as defined in step d) to afford an amide compound of formula XII.

f) Cyclizing a compound of formula XII using a metal base, such as potassium t-butoxide, sodium ethoxide, sodium methoxide, lithium ethoxide, and the like to afford a compound of formula XIII,

XIII wherein M+ is a metal cation from metals such as sodium, potassium, lithium, and the like.

g) Saponifying a compound of formula XIII followed by decarboxylation, and reducing the carbonyl group to give product Ia.

Route 2

A compound of formula I of the present invention, wherein R$^2$ and R$^3$ are hydrogen and R$^1$ is hydroxy (Ib), Ib can be prepared by a process which comprises the steps of:
a) Forming an anionic metal salt XIV by treating BMY-21502 with a strong metal base such lithium diisopropylamide, sodium hexamethyldisilizide, potassium hexamethyldisilizide, and the like; and b) Reacting said salt with an hydroxylating agent. A typical hydroxylating agent which can be used in the step is Davis reagent as described in "Reagents For Organic Synthesis," Vol. 11, Mary Fieser ed., John Wiley & Sons, Inc., N.Y., 108 (1984).

In formula XIV, $M^{30}$, is a metal cation as defined previously.

Route 3

Compounds of formula I of the present invention, wherein $R^1$ and $R^2$ are hydrogen and $R^3$ is hydroxy (Ic) and wherein $R^1$ and $R^2$ are hydrogen and $R^3$ is oxo (Id), can be prepared by a process which comprises the consecutive steps of:

a) Reacting succinimide (XV) with 4-chloromethylpyridine (XVI) in the presence of a base such as sodium hydride and the like to afford compound XVII.

b) Catalytically hydrogenating the pyridinyl group in compound XVII to yield compound XVIII c) Reacting compound XVIII with 4-chloro-2-(trifluoromethyl)pyrimidine (IV) in the presence of a base, such as sodium carbonate, sodium hydroxide, potassium hydroxide, and the like to afford Id.

d) Selectively reducing, preferably by using lithium borohydride, one carbonyl group in compound Id to afford Ic.

Route 4

Compound II of the present invention can be made by a process which comprises the consecutive steps of:

a) Condensing an alkyl formate of formula XX with an alkyl benzyloxyacetate of formula XIX with a metal base such as sodium hydride, potassium hydride, lithium hydride, and the like to afford a salt of formula XXI, wherein R and $M^+$ are as defined previously and Bz refers to a benzyl group with substituted or unsubstituted phenyl ring.

b) Reacting a salt of formula XXI with trifluoroacetamidine (XXII) to give hydroxypyrimidine XXIII

XXII    XXIII c) Chlorinating compound XXIII using a chlorinating reagent such as phosphorus oxychloride to afford compound XXIV.

XXIV d) Reacting compound XXIV with 1-[(4-piperidinyl)-methyl]-2-pyrrolidinone (XXV) in the presence of a base such as sodium carbonate and the like to afford compound XXVI.

XXV                    XXVI e) Removing the benzyl protecting group in compound XXVI by hydrogenolysis to afford product II.

Route 5

Compound III of the present invention can be made

III by a process which comprises the consecutive steps of:

a) Reacting 4-piperidone (XXVII) with 4-chloro-2-(trifluoromethyl)pyrimidine (IV) in the presence of a base such as sodium carbonate and the like to afford compound XXVIII.

XXVII

IV

XXVIII b) Converting compound XXVIII into epoxide XXIX. The process can be achieved by employing a base such as sodium hydride and an epoxidizing agent such as trimethyl oxosulfonium chloride.

XXIX c) Reacting epoxide XXIX with a metal salt of 2-pyrrolidinone of formula XXX to afford product III,

XXX wherein M+ is as defined previously.

Isolation and Structural Assignment of Metabolites

Five urinary and two plasma metabolites were isolated using HPLC conditions as described in the Description of Specific Embodiments section. Their structures are shown below. The structural determination was done by comparison of HPLC retention times with authentic samples and/or by spectral analysis.

Urinary Metabolites

Ie

-continued

If

Ig

Ia

Ic

Plasma Metabolites

Id

Ic

It is to be understood that the present invention is considered to include the various stereoisomers, e.g., optical isomers including individual enantiomers, mixtures of enantiomers, diastereomers, and mixtures of diastereomers, which can arise as a consequence of structural asymmetry due to the presence of one or two asymmetric carbon atoms which may be incorporated in some compounds of the instant series. Separation of the individual isomers is accomplished by application of various methods which are well known to practitioners in the art. For medicinal use, the pharmaceutically acceptable acid addition salts, those salts in which the anion does not contribute significantly to toxicity or pharmacological activity of the organic cation may be preferred in some cases. The acid addition salts are obtained either by reaction of an organic base of structures I, II, and III with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acids; phosphoric acids; and the like. Additionally, the present invention also encompasses any of formula I, II, and III compounds existing in solvate form such as a hydrate.

Compounds of the instant invention have been evaluated for cerebral function enhancing activity using as a primary screen the reversal of electroconvulsive shock (ECS)-induced amnesia for a step-down passive avoidance response [cf: Banfis, et al., J. Pharmacol. Meth., 8, 255 (1982); Janvik, Ann, Rev. Psychol., 23 457 (1972); and McGaugh and Petrinovich, Int. Rev. Neurobiology, 8, 139 (1965)]. Reference compounds such as pramiracetam, piracetam, aniracetam, etc., having activity in this paradigm have been purported to affect memory processes and may be useful in treating various dementias due to degenerative processes or diseases such as Alzheimer's disease. The following section describes the test method.

BIOLOGICAL PROCEDURES

In the test, rats were trained to remain immobile to avoid electric foot shock. Two control groups were required: an ECS control and a sham-ECS (no ECS) control. ECS control animals were placed individually on a platform over an activated shock grid 30 minutes after vehicle or experimental drug administration. The animals readily stepped down from the platform, immediately experienced the foot shock, and quickly learned to escape to the platform. An animal was considered to have acquired the passive avoidance response if it remained on the platform for 2 minutes without stepping down following the foot shock delivery. Immediately after the acquisition, the ECS control animals were delivered ECS via oracular electrodes at an intensity of 75 mA for 800 msec. The sham-ECS control animals were treated in a manner indentical to that described for the ECS controls, with the exception that current was not passed through the oracular electrodes. Both groups were administered a retention test 21 hours later. Animals were placed individually on the platform, and the latency to step down from the platform onto the unactivated shock grid was recorded; a given subject animal was considered to have retained the passive avoidance response if it remained on the platform for 120 seconds without stepping down. In general, vehicle treated rats not receiving ECS showed definite retention of response (83.5%), while vehicle treated animals receiving ECS displayed amnesia (17.5%) with regard to their ability to remember that descending the platform would result in a footshock. The active test compound were able to reverse the amnesiac effects of the ECS.

The quantal results are presented in both fractions and percentages and are accompanied by using the following ratio:

$$\frac{\text{Number of animals retaining}}{\text{Number of animals tested}}$$

Percentages are expressed as the percentage of sham-ECS control performance which was assigned an arbitrary value of 100 using the following formula:

$$\frac{\% \text{ of observed retraining animals}}{\% \text{ of observed retaining sham-}ECS \text{ control}} \times 100$$

Statistical comparisons were made using the 2×2 chi square formula corrected for one degree of freedom.

Table I shows the results of ECS tests.

TABLE I

| Compound | Retention of a Passive Avoidance Response after ECS-Induced Amnesia | | | | | |
|---|---|---|---|---|---|---|
| | Dose, mg/kg | | | | | |
| | 0.03 | 0.1 | 1.0 | 10 | 30 | Route |
| BMY-21502 | 36 (3/10)* | 64** (8/15) | 19(3/19) | 0(0/15) | 9 | PO |
| Id | | 24(2/10) | 28(3/13) | 24(2/10) | | PO |
| | | 65** (7/13) | 53(4/19) | 55** (6/13) | 48 (4/10) | SC |
| III | | 30(3/12) | 53(4/9) | 60(4/8) | | PO |
| II | | 33(3/11) | 48(4/10) | 54(5/11) | 51 | SC |
| Ic | | 54(5/11) | 34(4/14) | 33(3/11) | | PO |
| | | 28(3/13) | 22(2/11) | 48(4/10) | 13 (1/9) | SC |

*(Number of animals retaining/number of animals tested)
**p ≦ 0.05
Sham - ECS/Controls = 100%
Vehicle - ECS controls = 21%

Foregoing results indicate that the compounds of formula I, II, and III are found to be useful in preventing amnesia which results from electroconvulsive shock. Such activity not only relates to memory retention in normal aging and senility processes but would be useful in protecting against the amnesia-producing effects of electroconvulsant shock as it is used clinically. Electroconvulsant shock is employed to treat some classes of psychiatric patients, particularly depressed patients who are refractory to traditional pharmacologic therapy. It is well documented that these electroconvulsant shock treatments induce the undesirable side-effect of amnesia in those patients to whom it is administered. The instant compounds which exhibit activity in protecting against the amnesia-producing effects of electroconvulsant shock in pharmacologic testing would be useful adjuncts to the clinical use of electroconvulsant shock in psychiatric treatment.

Further consideration of test results obtained for compounds of the present invention indicates their usefulness in several specific applications wherein such psychocognitive enhancement or normalizing effects on cerebral function would be highly desirable. The subject compounds are intended to be useful in treatment of dementias due to degenerative processes, diseases, and the like; with some specific examples being age-related memory dysfunction; AIDS-related dementia; multiple infarct dementia; Alzheimer's disease; Parkinson-related dementia; and the like. Similarly, the compounds are useful in enhancement of memory and learning processes and for acquisition of new information as well as treating deficits such as those encountered in benign senescent forgetfulness, learning disabilities and certain retardation states, e.g. minimal brain dysfunction. The compounds are also useful as antiamnesiacs and would find application against amnesias whether induced by ECS (a standard antidepressant treatment); drugs, e.g. benzodiazepines, alcohol, etc.; or trauma, e.g. head injury, post-neurosurgery, and so forth. Other uses which are envisioned for the compounds of this invention would be to treat miscellaneous disorders such as dyslexia, aphasia, and Tourette's syndrome.

In summary of the foregoing discussion, the instant compounds have cerebral function enhancing properties particularly suited to their use in treating dementias cognition and memory enhancement, reversal and/or prevention of amnesia and certain miscellaneous applications. Thus, another aspect of the instant invention concerns a process for enhancing cerebral function in a mammal in need of such treatment which comprises systemic administration to such mammal of an effective dose of a formula I, II or III compound or a pharmaceutically acceptable acid addition salt thereof. The administration and dosage regimen of compounds of formula I, II and III is considered to be done in the same manner as for the reference compound piracetam, cf: Reisberg, et al., in Drug Development Research, 2475-480 (1982); Weng et al., in Rational Drug Therapy, 17(5), 1-4 (1983); Reisberg, et al., in Psychopathology in the Aged", Editors, Cole and Barrett, Raven Press, New York, 243-245 (1980) and pramiracetam, cf: Butler, et al., J. Med. Chem., 27, 684-691 (1984).

The mode of systemic administration, dosage, and dosage regimen must in each case be carefully adjusted by utilization of sound professional judgment and consideration of the age, weight and condition of the recipient. Generally, the daily dose will be from about 0.1 g to about 10 g, preferably 0.5 g to 5 g, when given orally. In some instances, a sufficient therapeutic effect can be obtained at lower doses while in other, larger doses will be required. As is apparent to one skilled in clinical pharmacology, the amount of a formula I, II, or III compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that when a compound of the present invention is administered orally which is the preferred route, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective cerebral function enhancing amount of a compound of formula I, II, or III or a pharmaceutically acceptable acid addition salt thereof and a pharmaceutically acceptable carrier. Pharmaceutical compositions for effecting such treatment will contain a major or minor amount (e.g. from 95% to 0.5%) of at least one compound of the present invention in combination with pharmaceutical carrier, the carrier comprising one or more solid, semi-solid, or liquid diluent, filler and formulation adjutant which is non-toxic, inert and pharmaceutically acceptable. Such pharmaceutical compositions are preferably in dosage unit forms; i.e. physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents, (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a formula I, II, or III compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF SPECIFIC EMBODIMENTS

Collection of Urine Samples

Four dogs were given a 50 mg/kg dose of BMY-21502 orally and urine samples were collected from 0-6 hr and 6-24 hr. The samples were immediately frozen until analysis. The 0-6 and 6-12 hr samples were combined in equal volumes prior to beginning the isolation procedure.

HPLC Conditions for Urine Sample Analysis

Three different HPLC systems were used to isolate and characterize the metabolites: a reverse-phase, a partition and a normal-phase.

a. Reverse-phase System. This system consisted of an analytical µBondapak Phenyl column (Waters, 3.9×300 mm) with a mobile phase consisting of methanol/water (50:50) at a flow rate of 1.0 mL/min. In this as well as the systems below, the injector was a Waters U6K, and detection was by U.V. absorbance at 254 nm.

b. Partition System. This system consisted of an analytical column packed with Zorbax silica (DuPont, 3.9×300 mm) with a mobile phase consisting of acetonitrile/0.01 M ammonium acetate, pH 5.0, at 98/2 with a flow rate of 1.0 mL/min. This was used to establish retention times of standards and metabolites. It was also employed with a modified mobile phase of acetonitrile/water at 99/1 and a semi-preparative silica column (9.4×250 mm) to effect the preparative separation of peak 2 from the reverse-phase system into two peaks (vide infra).

c. Normal-phase System. This system consisted of an analytical Zorbax silica column (DuPont, 4.6×250 mm) with a mobile phase consisting of acetonitrile in pump A, and ethanol/water/methanesulfonic acid (100:1:0.1) in pump B. The mobile phase was 70% A and the flow rate was 1.0 mL/min.

Isolation of Urinary Metabolites

Figure 1:
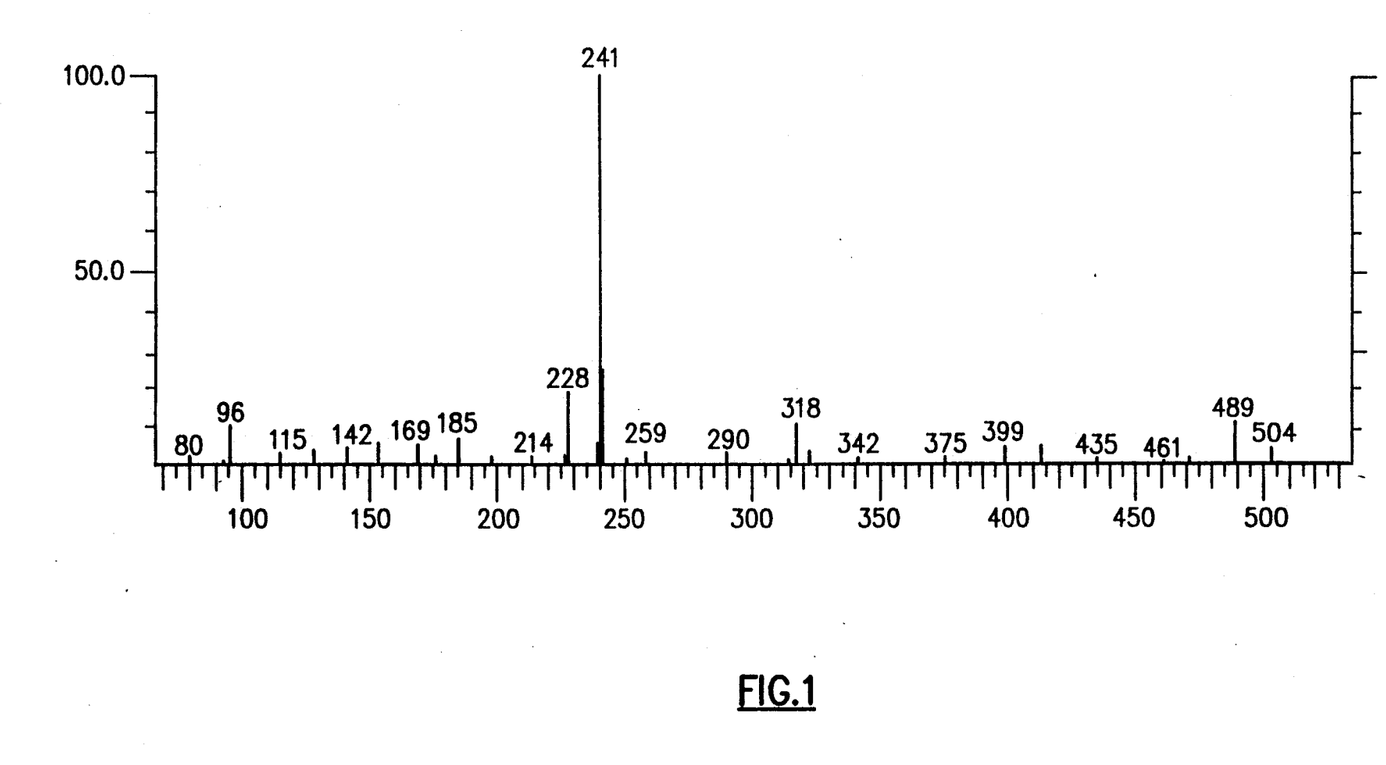
FIG. 1. EI mass spectrum of TMS derivative of a dog urinary BMY-21502 metabolite from peak 1.
Figure 2:
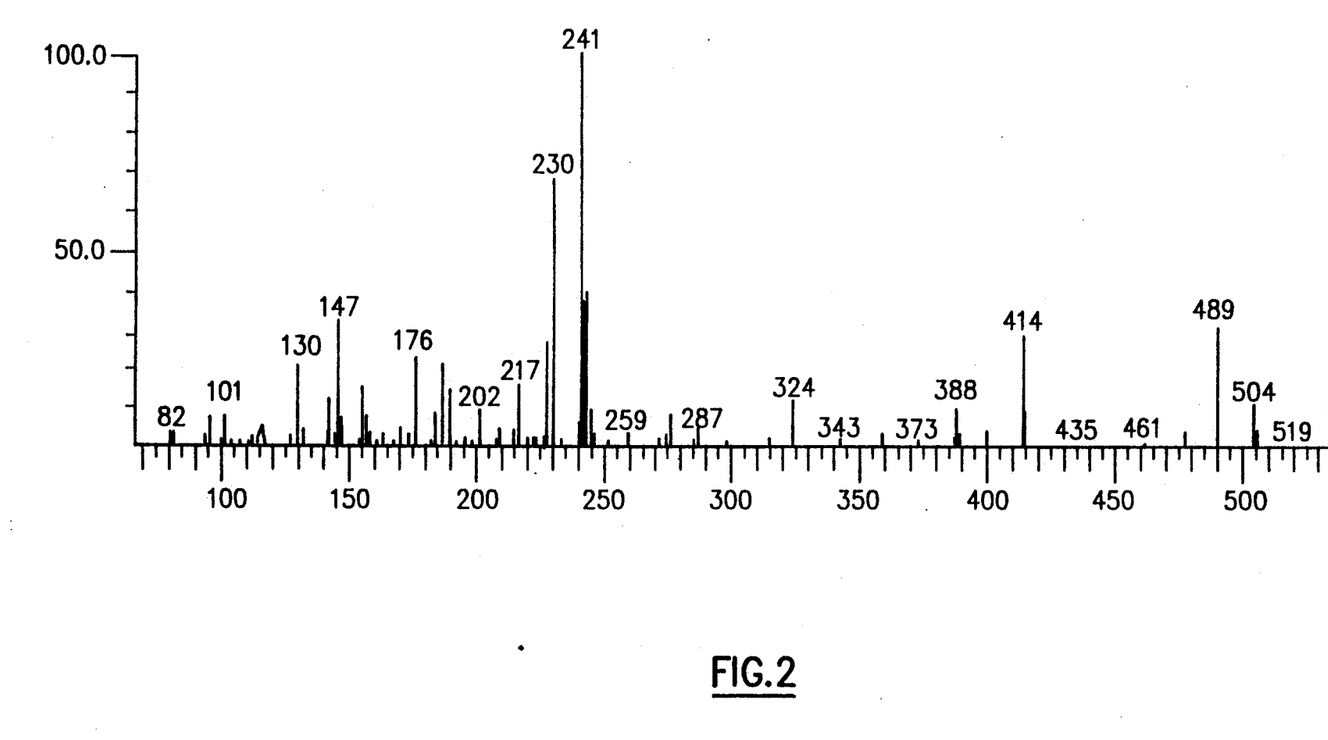
Figure 3:
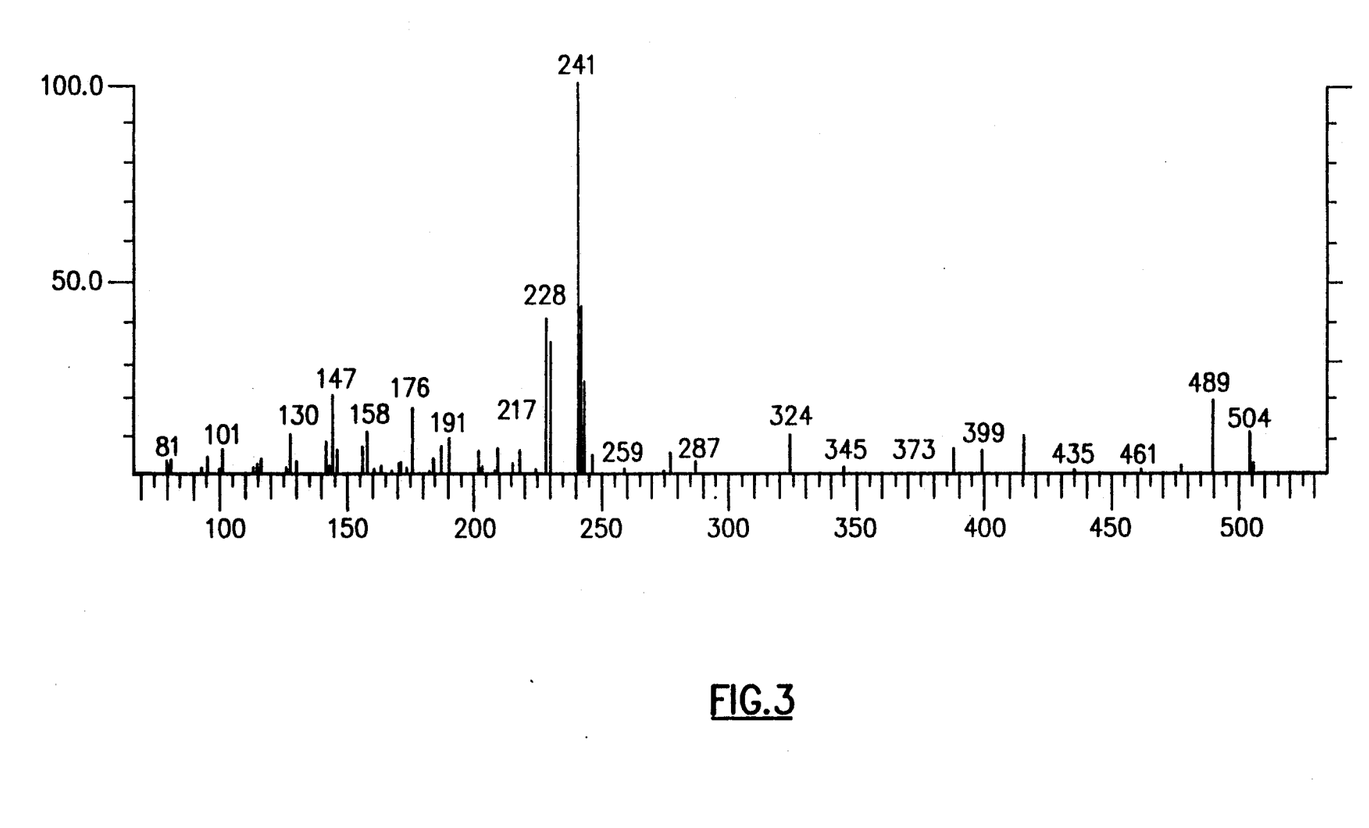
FIG. 3. EI mass spectrum of TMS derivative of a dog urinary BMY-21502 metabolite from peak 2b.

Urine samples obtained from dogs as described above were prepared for chromatography by the addition of an equal volume of methanol to the sample, followed by centrifugation to remove insoluble matter. The samples were filtered through a 5µ filter prior to injection. The samples were repeatedly injected onto the reverse-phase HPLC system which afforded four peaks of retention times of approximately at 5.6, 6.3, 7.5, and 8.2 minutes. The peaks were collected from each injection and the peaks 1-4 from all the injections were individually pooled. By repeated chromatography, it was possible to obtain approximately 130 µg of peak 1, 340 µg of peak 2, 35 µg of peak 3, and 350 µg of peak 4 from approximately 2 mL of urine. It was subsequently observed upon further HPLC analysis that peak 2 consisted of two approximately equal components, which were resolved by further HPLC in the semi-preparative partition system into peaks 2a and 2b, eluting at 9.7 and 11.1 min. FIGS. 1-3 are mass spectra of metabolites from peaks 1, 2a, and 2b.

Metabolites from peaks 1, 2a, and 2b were identified as all three possible isomers of dihydroxy-1-[[1-[2-(trifluoromethyl)-4-pyrimidinyl]-4-piperidinyl]methyl]-2-pyrrolidinone (Ie-Ig). On the other hand, metabolites from peaks 3 and 4 were found to be 4-hydroxy-1-[[1-[2-(trifluoromethyl)-4-pyrimidinyl]-4-piperidinyl]methyl]-2-pyrrolidinone (Ia) and 5-hydroxy-1-[[1-[2-(trifluoromethyl)-4-pyrimidinyl]-5-piperidinyl]methyl]-2-pyrrolidinone (Ic), respectively.

Isolation of Plasma Metabolites

HPLC of methyl t-butyl ether extract of plasma taken from a dog dosed at the 200 mg/kg level afforded two metabolites with retention times between 4.4-5.8 min and 7.0-8.0 min. The HPLC condition used was as follows:
HPLC Column: Phenyl-RP, 4.5 mm×150 mm, 5 µm particle size column from Jones Chromatography fitted with Upchurch C130 precolumn packed with Whatman Co-Pell ODS;
Mobile Phase: 25% acetonitirle, 5% methanol in 0.05 M ammonium acetate, pH 5.3;
Flow Rate: 1.5 mL/min; Detection: UV at 260 nm.
The two metabolites thus obtained were identified as compounds Ic and Id.

The compounds which constitute this invention and their methods of preparation will appear more fully from a consideration of the following examples which are given for the purpose of illustration only and are not to be construed as limiting the invention is sphere or scope. All temperatures are understood to be in degrees C when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), employed are DMSO-$d_6$ (perdeuterodimethysulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory elemental analyses.

EXAMPLE 1

1-[2-(Trifluoromethyl)-4-pyrimidinyl]-4-piperidinecarboxamide (VI)

A mixture of 4-chloro-2-(trifluoromethyl)pyrimidine (IV, 23.66 g, 0.130 mol), isonipecotamide (V, 16.66 g, 0.130 mol), and sodium carbonate (27.56 g, 0.260 mol) in acetonitrile (250 mL) was refluxed for 4 hr. The mixture was cooled and a solid mass formed. This mass was dissolved in DMF (300 mL) and filtered to remove the inorganics. The solvent was removed in vacuo and the crude product was recrystallized from isopropanol and then from 90% ethanol to give colorless needles (24.8 g, 70%).

EXAMPLE 2

1-[2-(Trifluoromethyl)-4-pyrimidinyl]-4-piperidinecarbonitrile (VII)

Phosphorus oxychloride (22 mL) was added with stirring to DMF (220 mL). The exothermic reaction mixture turned deep red, and compound VI (23.20 g, 85 mmol) was added. The mixture was cooled in a water bath and stirred for 20 hr. The DMF was then removed under vacuum and the residue was dissolved in methylene chloride (300 mL). Saturated aqueous sodium carbonate (ca 200 mL) was added to the solution with ice bath cooling until no more bubbling was observed. The methylene chloride layer was separated and concentrated in vacuo. The residue was recrystallized from hexanes-ethyl acetate to give the crystalline product (19.0 g, 87%).

EXAMPLE 3

[[1-[2-(Trifluoromethyl)-4-pyrimidinyl]-4-piperidinyl]methyl]amine (VIII)

A solution of VII (19.0 g, 74.2 mmol) in methanol (150 mL) and ammonium hydroxide (50 mL of a 30% solution) was hydrogenated over a Raney nickel catalyst (ca 5 g) at 60 psi for 30 hr. The mixture was filtered and concentrated in vacuo to give the product as a light green oil (19.40 g, 100%).

EXAMPLE 4

Ethyl [[1-[2-(trifluoromethyl)-4-pyrimidinyl]-4-piperidinyl]methyl]aminoacetate (Xa)

Ethyl bromoacetate (2.35 mL, 21.2 mmol) was added to a mixture of XII (5.0 g, 19.2 mmol) and potassium carbonate (5.32 g, 38.5 mmol) in acetonitrile (65 mL). After stirring for 20 hr, the mixture was filtered and concentrated in vacuo. The residue was chromatographed on silica gel using 5% methanol-ethyl acetate as the eluent to give the product (4.03 g, 61%).

EXAMPLE 5

Ethyl 3-[[N-(ethoxy-2-oxoethyl)-N-[1-[2-(trifluoromethyl)4-pyrimidinyl]-4-piperidinyl]methyl]amino]-3-oxopropanoate (XIIa)

Ethyl malonyl chloride (3.0 mL, 23.2 mmol) was added dropwise to a mixture of Xa (4.03 g, 11.6 mmol) and potassium carbonate (3.5 g, 25 mmol) in acetonitrile (75 mL). After stirring for 20 hr, the mixture was filtered and concentrated in vacuo. The residue was chromatographed on silica gel using ethyl acetate to give the title product (5.05 g, 94%).

EXAMPLE 6

Ethyl 2,5-dihydro-4-hydroxy-2-oxo-1-[[1-[2-(trifluoromethyl)-4-pyrimidinyl]-4-piperidinyl]methyl]-3-pyrrolecarboxylate, potassium salt (XIIIa)

Potassium tert-butoxide (1.47 g, 13.1 mmol) was added to a solution of XIIa (5.05 g, 10.9 mmol) in absolute ethanol (70 mL). The solution started as clear, but became cloudy after 10 min. The mixture was refluxed for 2 hr and then stirred at room temperature for 16 hr. The mixture was cooled in an ice bath and the product collected as a white precipitate (3.36 g, 68%).

EXAMPLE 7

4-Hydroxy-1-[[1-[2-(trifluoromethyl)-4-pyrimidinyl]-4-piperidinyl]methyl]-2-pyrrolidinone (Ia)

A solution of XIIIa (1.0 g, 2.5 mmol) in acetonitrile (10 mL) and water (0.058 mL) was placed in a preheated oil bath, refluxed for 20 min, and then cooled in an ice bath. Ethanol (15 mL) and sodium borohydride (0.10 g, 2.5 mmol) were added and the solution was stirred for 18 hr at room temperature. The solvent was removed in vacuo. The residue was dissolved in ethyl acetate and filtered. The filtrate was concentrated in vacuo and the residue was chromatographed on silica gel using 10% methanol-ethyl acetate as the eluent to give the product as a white powder (0.68 g, 79%).

NMR (CDCl$_3$): 1.14–1.30 (m, 2 H), 1.7–1.8 (m, 2 H), 1.9–2.05 (m, 1 H), 2.35 (d of d, 1 H, J=2.1 and 17.3 Hz), 2.66 (d of d, 1 H, J=6.3 and 17.3 Hz), 2.92 (t, 2 H, J=11.7 Hz), 3.07 (d of d, 1 H, J=7.1 and 13.7 Hz), 2.2–2.3 (broad s, 1 H, OH), 3.24–3.35 (m, 2 H), 3.62 (q, 1 H, J=5.4 Hz), 4.1–4.7 (broad s, 2 H, 2-CH), 4.45–4.55 (m, 1 H), 6.53 (d, 1 H, J=6.4 Hz), 8.19 (d, 1 H, J=6.4 Hz).

IR(KBr): 3355, 2926, 1670, 1598, 1508, 1337 cm$^{-1}$.

EXAMPLE 8

3-Hydroxy-1-[[1-[2-(trifluoromethyl)-4-pyrimidinyl]-4-piperidinyl]methyl]-2-pyrrolidinone (Ib)

n-Butyl lithium (3.1 ml of 2.14 M, 6.63 mmole) was added to a stirred solution of hexamethyldisilazane (1.4 ml, 6.64 mmole) in THF (15 ml) at −40° C. The solution was cooled to −78° C., a −78° C. solution of BMY-21502 (2.0 g, 6.10 mmole) in THF (60 ml) was added, and the solution was stirred (−78° C., 1.5 hr). A solution of 3-phenyl-2-benzenesulfonyloxaziridine (2.41 g, 9.20 mmole) in THF (15 ml) was added, and the solution was allowed to warm to room temperature over 18 hr. with stirring. The reaction was quenched with saturated NH₄Cl (50 ml) and extracted with ether three times. The ether extracts were dried over MgSO₄, filtered, and concentrated in vacuo. The residue was chromatographed on silica gel using a 3 to 4% methanol/CH₂Cl₂ gradient as the eluent to give the product as a yellow foam (yield 370 mg, 18%).

NMR (CDCl₃):δ 1.14–1.30 (m, 2 H), 1.65–1.80 (m, 2 H), 1.88–2.05 (m, 2 H), 2.35–2.50 (m, 1 H), 2.90 (t, 2 H, J=12.2 Hz), 3.14–3.20 (m, 2 H), 3.25–3.45 (m, 2 H), 4.35 (t, 1 H, J=8.1 Hz), 4.2–5.0 (broad s, 3 H), 6.52 (d, 1 H, J=6.2 Hz) 8.20 (d, 1 H, J=6.2 Hz).

IR (KBr): 3406, 2932, 1684, 1598, 1146 cm$^{-1}$.

Analysis for $C_{15}H_{19}N_4O_2F_3 \cdot 0.1$ H₂O: Calcd: C:52.06; H:5.60; N:16.19 Found: C:52.32; H:5.47; N:15.83.

EXAMPLE 9

1-(4-Pyridinylmethyl)-2,5-pyrrolidinedione (XVII)

A suspension of sodium hydride (17.6 g, 0.44 mol) in DMF (500 mL) was stirred with ice bath cooling as succinimide (29.73 g, 0.3 mol) was cautiously added. 4-Picolyl chloride hydrochloride (32.81 g, 0.2 mol) was then added cautiously with vigorous stirring. The mixture was stirred at room temperature for 1 day and then at 100° C. for 2 days. The mixture was then cooled and filtered. The filtrate was concentrated in vacuo to give a black oil. This dark crude product was stirred four times with boiling cyclohexane (150 mL), each time decanting the boiling cyclohexane from the dark residue. Upon cooling the cyclohexane extracts, the desired product crystallized as colorless needles (23.05 g, 60.9%) which were filtered and air dried.

EXAMPLE 10

1-[(4-Piperidinyl)methyl]-2,5-pyrrolidinedione hydrochloride (XVIII)

A suspension of platinum oxide (0.3 g), in a solution of XVII (16.71 g, 88 mmol) in ethanol (100 mL) and concentrated HCl (17.6 g, 176 mmol), was hydrogenated in a 500 mL Parr bottle at 60 psi and room temperature for 24 hr. The mixture was then filtered. The filtrate was concentrated in vacuo to give the product as a white powder which was used in the next step without further purification.

EXAMPLE 11

1-[[1-[2-(Trifluoromethyl)-4-pyrimidinyl]-4-piperidinyl]methyl]-2,5-pyrrolidinedione hydrate (Id)

Sodium carbonate (30 g, 0.28 mol) was added to a solution of XVIII in water (250 mL). The solution was then vigorously stirred with ice bath cooling as 4-chloro-2-(trifluoromethyl)-pyrimidine (IV, 16.06 g, 88 mmol) was added. The mixture warmed to room temperature over a 24 hr period, and the desired product was formed as a white precipitate (21.76 g, 73.3%, mp: 144°–145° C.) which was collected, washed with water, and dried.

NMR(CDCl₃) δ 1.05–1.3 (m, 2 H), 1.70 (d, 2 H, J=12.7 Hz), 1.95–2.07 (m, 1 H), 2.70 (s, 4 H), 2.87 (t, 2 H, J=11.8 Hz), 3.40 (d, 2 H, J=7.1 Hz), 4.42 (broad s, 2 H), 6.51 (d, 1 H, J=6.3 Hz), 8.20 (d, 1 H, J=6.3 Hz).

IR (KBr): 1740, 1698, 1595, 1555, 1510, 1455, 1370 cm$^{-1}$.

Analysis for $C_{15}$ $H_{17}$ $N_4$ $O_2$ $F_3 \cdot 0.05$ H₂O: Calc: C: 52.50; H: 5.03; N: 16.33; H₂O: 0.26; Found: C: 52.53; H: 4.93; N: 16.28; H₂O: 0.12.

EXAMPLE 12

5-Hydroxy-1-[[1-[2-(trifluoromethyl)-4-pyrimidinyl]-4-piperidinyl]methyl]-2-pyrrolidinone hydrate (Ic)

Lithium borohydride (2.39 g, 0.110 mol) was added with stirring and ice bath cooling to a solution of Id (7.52 g, 22 mmol) in anhydrous THF (100 mL). The mixture was stirred with ice bath cooling for 1 hr and then at room temperature for 7 hr. The solution was then cooled in an ice bath as the excess lithium borohydride was cautiously quenched with acetone (75 mL). The mixture was concentrated in vacuo, and the residue chromatographed on silica gel using a gradient of ethanol (0 to 20%) in ethyl acetate as the eluent. The product was obtained as a white powder (6.46 g, 85.4%, mp: 105°–108°).

NMR (CDCl₃): δ 1.12–1.3 (m, 2 H), 1.68–2.10 (m, 4 H), 2.15–2.40 (m, 2 H), 2.48–2.65 (m, 1 H), 2.90 (t, 2 H, J=12.8 Hz), 3.09 (d of d, 1 H, J=13.8 & 6.9 Hz), 3.32 (d of d, 1 H, J=13.8 & 7.8 Hz), 3.71 (d, 1 H, J=7.9 Hz), 4.41 (broad s, 2 H), 5.18 (t, 1 H, J=6.1 Hz), 6.53 (d, 1 H, J=6.3 Hz), 8.19 (d, 1 H, J=6.3 Hz).

IR: 3240, 1675, 1605, 1340, 1150 cm$^{-1}$.

Analysis for $C_{15}H_{19}N_4O_2F_3 \cdot 0.1$ H₂O: Calc: C: 52.06; H: 5.60; N: 16.19; H₂O: 0.52; Found: C: 52.30; H: 5.61; N: 16.09; H₂O: 0.54.

EXAMPLE 13

1-[2-(Trifluoromethyl)-4-pyrimidinyl]-4-piperidone (XXVIII)

4-Piperidone monohydrate hydrochloride (XXVII, 3.37 g, 21.9 mmol) was added to a stirred mixture of methylene chloride (50 mL) and saturated aqueous sodium carbonate (8 mL). 4-Chloro-2-(trifluoromethyl)-pyrimidine (IV, 4.0 g, 21.9 mmol) was then added to the mixture which was then stirred for 2 days. The organic layer was separated, dried over magnesium sulfate, and concentrated in vacuo to give the product as a white solid (4.9 g, 92%) which was used in the next step without further purification.

EXAMPLE 14

6-[2-(Trifluoromethyl)-4-pyrimidinyl]-1-oxa-6-azaspiro[2.5]-octane (XXIX)

Sodium hydride (0.48 g of 60% mineral oil dispersion, 12 mmol) in a round bottom flask was washed free of the mineral oil with hexanes before DMSO (20 mL, distilled from calcium hydride) was added. Trimethyloxosulfonium chloride (1.54 g, 12 mmol) was added and the mixture was stirred under dry nitrogen for 20 min at room temperature. A solution of XXVIII (2.45 g, 10 mmol) in DMSO (5 mL) was then added to this milky suspension. The mixture was stirred at room temperature for 30 min, and then heated in a 50° C. oil bath for 1 hr. The reaction was quenched with water (30 mL) and extracted with ether (3×60 mL). The ether extracts were washed with water (3×15 mL), dried over sodium sulfate, and concentrated in vacuo to give the product as a white solid (2.1 g, 81%).

EXAMPLE 15

1-[[4-Hydroxy-1-[2-(trifluoromethyl)-4-pyrimidinyl]-4-piperidinyl]methyl]-2-pyrrolidinone (III)

Potassium tert-butoxide (1.03 g, 9 mmol) was added to a solution of 2-pyrrolidinone (0.7 g, 7.7 mmol) in anhydrous DMF (25 mL). The mixture was stirred for 45 min at room temperature to produce a milky white precipitate. A solution of XXIX (2.0 g, 7.7 mmol) in dry DMF (6 mL) was then added and the mixture slowly turned clear as it was stirred for 18 hr. The mixture was concentrated in vacuo and the residue chromatographed on neutral alumina using ethyl acetate as the eluent to give the white solid product (0.40 g, 35%, mp: 170°-172° C.).

NMR(CDCl$_3$): δ 1.55 (d or t, 2 H, J=5 & 12 Hz), 1.7–1.85 (m, 2 H), 2.05–2.23 (m, 2 H), 2.48 (t, 2 H, J=7 Hz), 3.34 (s, 2 H), 3.45 (d or t, 2 H, J=3 & 12 Hz) 3.55 (t, 2 H, J=7 Hz), 4.0–4.6 (broad s, 3 H, 2 CH & 1 OH), 6.60 (d, 1 H, J=6 H), 8.26 (d, 1 H, J=6 H).

IR(KBr): 1662, 1607, 1341, 1149, 1133 cm$^{-1}$.

Analysis for $C_{15} H_{19} N_4 F_3 O_2$·0.1 EtOAc·0.2 H$_2$O: Calcd: C:51.85; H: 5.61; N: 15.71; Found: C: 15.50; H: 5.56; N. 15.88.

EXAMPLE 16

Ethyl 2-benzyloxy-formylacetate, sodium salt (XXIa)

Sodium hydride (2.92 g of a 60% mineral oil dispersion, 73 mmol) was washed free of the mineral oil with hexanes and resuspended in toluene (100 mL). Ethyl formate (2.92 g, 73 mmol) was added to the mixture followed by ethyl 2-benzyloxyacetate (14.2 g, 73 mmol). The mixture was stirred under nitrogen for 3 days and then the precipitate was collected and dried in vacuo (6.8 g, 38%).

EXAMPLE 17

5-Benzyloxy-4-hydroxy-2-(trifluoromethyl)pyrimidine (XXIII)

A solution of trifluoroacetamidine (XXII, 3.14 g, 27.8 mmol) and XXIa (6.8 g, 27.8 mmol) in ethanol (60 mL) was refluxed for 18 hr. The mixture was cooled and concentrated in vacuo. The residue was dissolved in a minimal volume of water and the solution was acidified with concentrated HCl. The product was obtained as a white precipitate (3.3 g, 44%)

EXAMPLE 18

5-Benzyloxy-4-chloro-2-(trifluoromethyl)pyrimidine (XXIV)

A mixture of XXIII (3.3 g, 12.2 mmol), diethyl aniline (1.94 mL, 12.2 mmol), and phosphorus oxychloride (0.758 mL, 8.13 mmol) was heated in a 100° C. oil bath for 3 hr. The dark reaction mixture was vacuum distilled to give the product as a clear oil (1.0 g, 28.4%).

EXAMPLE 19

1-[[1-[5-(Phenylmethoxy)-2-(trifluoromethyl)-4-pyrimidinyl]-4-piperidinyl]methyl]-2-pyrrolidinone (XXVI)

A mixture of 1-[(4-piperidinyl)methyl]-2-pyrrolidinone hydrate (XXV 0.63 g, 3.46 mmol), compound XXIV (1.0 g, 3.46 mmol), and sodium carbonate (0.8 g, 6.92 mmol) in acetonitrile (20 mL) was refluxed for 18 hr. The mixture was cooled, filtered, and concentrated in vacuo. The residue was chromatographed on silica gel using ethyl acetate as the eluent to give the desired product (1.2 g, 79.8%, mp: 155°-157°).

NMR (CDCl$_3$): δ 1.2–1.35 (m, 2 H), 1.67 (d, 2 H, J=13 Hz), 1.85–2.0 (m, 1 H), 1.95–2.1 (m, 2 H), 2.38 (t, 2 H, J=8 Hz), 2.92 (t, 2 H, J=13 Hz), 3.15 (d, 2 H, J=7 Hz), 3.37 (t, 2 H, J=7 Hz), 4.72 (d, 2 H, J=14 Hz), 5.09 (s, 2 H), 7.3–7.4 (m, 5 H), 7.91 (S, 1 H).

IR(KBr): 1688, 1591, 1273, 1260, 1237, 1195, 1138 cm$^{-1}$.

Analysis for $C_{22} H_{25} N_4 O_2 F_3$: Calcd: C: 60.82; H: 5.80; N: 12.90; Found: C: 60.91; H: 5.78; N: 12.82.

EXAMPLE 20

1-[[1-[5-hydroxy-2-(trifluoromethyl)-4-pyrimidinyl]-4-piperidinyl]methyl]-2-pyrrolidinone (II)

A solution of XXVI (0.90 g, 2.1 mmol) in ethanol (75 mL) was hydrogenated with 10% Pd/C (0.20 g) at 60 psi for 2 hr. The mixture was filtered and concentrated in vacuo to give the product as a white powder (0.40 g, 54%, mp: 213°-215°).

NMR (CDCl$_3$): δ 1.0–1.25 (m, 2 H), 1.62 (d, 2 H, J=14 Hz), 1.85–2.05 (m, 3 H), 2.1–2.3 (m, 2 H), 2.90 (t, 2 H, J=12.6 Hz), 3.03 (d, 2 H, J=7.2 Hz), 3.25–3.45 (m, 2 H), 4.63 (d, 2 H, J=10.8 Hz), 7.80 (s, 1 H), 10.95 (broad s, 1 H).

IR(KBr): 3400, 1670, 1588, 1276, 1243, 1135, 961 cm$^{-1}$.

Analysis for $C_{15} H_{19} N_7 O_2 F_3$·0.1 EtOH·0.15 H$_2$O: Calcd: C: 51.92; H: 5.70; N: 15.94; Found: C: 51.59; H: 5.55; N: 15.74.

We claim:

1. The compound of formula I and its pharmaceutically acceptable salts thereof, wherein
$R^1$, $R^2$ and $R^3$ are independently selected from hydrogen and hydroxy
with the proviso that $R^1$, $R^2$, and $R^3$ cannot all be hydrogen or hydroxy at the same time.

2. A compound of Formula II and its pharmaceutically acceptable salts thereof

3. A compound of Formula III and its pharmaceutically acceptable salts thereof

4. The compound of claim 1, 3-hydroxy-1-[[1-[2-(trifluoromethyl)-4-pyrimidinyl]-4-piperidinyl]methyl]-2-pyrrolidinone.

5. The compound of claim 1,
4-hydroxy-1-[[1-[2-(trifluoromethyl)-4-pyrimidinyl]-4-piperidinyl]methyl]-2-pyrrolidinone.

6. The compound of claim 1,
5-hydroxy-1-[[1-[2-(trifluoromethyl)-4-pyrimidinyl]-4-piperidinyl]methyl]-2-pyrrolidinone.

7. The compound of claim 1,
3,4-dihydroxy-1-[[1-[2-(trifluoromethyl)-4-pyrimidinyl]-4-piperidinyl]methyl]-2-pyrrolidinone.

8. The compound of claim 1,
3,5-dihydroxy-1-[[1-[2-(trifluoromethyl)-4-pyrimidinyl]-4-piperidinyl]methyl]-2-pyrrolidinone.

9. The compound of claim 1,
4,5-dihydroxy-1-[[1-[2-(trifluoromethyl)-4-pyrimidinyl]-4-piperidinyl]methyl]-2-pyrrolidinone.

10. A method for enhancing cognition and memory in a mammal in need of such treatment which comprises systemic administration to the mammal of an effective dose of a compound claimed in claim 1.

11. A pharmaceutical composition in dosage unit form suitable for systemic administration to a mammalian host comprising a pharmaceutical carrier and cognition and memory enhancing amount of a compound claimed in claim 1.

12. A method for enhancing cognition and memory in a mammal in need of such treatment which comprises systemic administration to the mammal of an effective dose of the compound claimed in claim 2.

13. A pharmaceutical composition in dosage unit form suitable for systemic administration to a mammalian host comprising a pharmaceutical carrier and cognition and memory enhancing amount of the compound claimed in claim 2.

14. A method for enhancing cognition and memory in a mammal in need of such treatment which comprises systemic administration to the mammal of an effective dose of the compound claimed in claim 3.

15. A pharmaceutical composition in dosage unit form suitable for systemic administration to a mammalian host comprising a pharmaceutical carrier and cognition and memory enhancing amount of the compound claimed in claim 3.

* * * * *